United States Patent

Morgan et al.

[11] Patent Number: 5,910,106
[45] Date of Patent: Jun. 8, 1999

[54] METHOD AND APPARATUS FOR HEATING A SURGICAL INSTRUMENT

[75] Inventors: Shanon Morgan, Azle; Michael W. Keith, Watauga; Kevin P. Nelms, Denton; David Mills, Fort Worth, all of Tex.

[73] Assignee: Fieldtech Avionics and Instruments, Inc., Fort Worth, Tex.

[21] Appl. No.: 09/080,052

[22] Filed: May 15, 1998

[51] Int. Cl.⁶ .................................................. A61B 1/06
[52] U.S. Cl. ..................................... 600/169; 126/263.05
[58] Field of Search ................................... 600/101, 102, 600/104, 133, 151, 156, 169; 126/263.04, 263.05, 263.07, 263.08, 263.09

[56] References Cited

U.S. PATENT DOCUMENTS

| | | | |
|---|---|---|---|
| 4,279,246 | 7/1981 | Chikama . | |
| 4,872,442 | 10/1989 | Manker | 126/263 |
| 5,172,683 | 12/1992 | West | 126/263 |
| 5,207,213 | 5/1993 | Auhll et al. . | |
| 5,351,675 | 10/1994 | Brodsky | 126/263 |
| 5,400,767 | 3/1995 | Murdoch | 600/157 |
| 5,503,149 | 4/1996 | Beavin . | |
| 5,549,543 | 8/1996 | Kim | 600/169 |
| 5,647,840 | 7/1997 | D'Amelio et al. . | |
| 5,651,757 | 7/1997 | Meckstroth | 600/169 |

*Primary Examiner*—Gene Mancene
*Assistant Examiner*—Ira Hatton
*Attorney, Agent, or Firm*—Richard K. Robinson

[57] ABSTRACT

An instrument heater for heating a surgical instrument. The instrument heater includes a sheath having an inner and outer wall. The inner wall forms a bore through which the optical scope is inserted. A chemical solution fills the space between the inner and outer wall of the sheath. At one end of the sheath is an activator disk having a chemical substance attached to its surface. When the activator disk is flexed, it ejects the chemical substance and interacts with the chemical solution to initiate an exothermic reaction. The exothermic reaction results in the generation of heat within the sheath, which is transmitted to the surgical instrument. Once the surgical instrument is sufficiently heated to a temperature close to the temperature of a body, the optical scope is inserted into the body. A natural tendency for the instrument to fog up is prevented by the equalizing the temperature of the instrument with the body.

17 Claims, 5 Drawing Sheets

METHOD AND APPARATUS FOR HEATING A SURGICAL INSTRUMENT

BACKGROUND OF THE INVENTION

1. Technical Field of the Invention

This invention relates to instrument heaters, and more particularly, to an apparatus for heating a instrument used in surgery, such as laparoscopic surgery.

2. Description of Related Art

Various delicate and small instruments are used in surgery. One of the most important instruments utilized by surgeons is an optical scope. An optical scope is essentially a telescope which normally has a camera for inserting through a small incision into a human body to view the interior of the body, such as the stomach. The optical scope includes a long thin cylindrical probe having a lens at one end and a fiber optic line that connects a camera to the lens. Wires connect the camera to a display used for viewing by a surgeon. The long thin portion of the probe is small enough and long enough to enter through the small incision. The use of the optical scope provides a very useful means for viewing the interior of the human body, without opening the cavity of a body to major surgery (e.g., large incisions).

Although the optical probe is very useful in surgery, there is a problem associated with using the optical scope. When the optical scope is initially inserted through the small incision into the interior of the body, the lens at the tip of the optical scope fogs up. The optical scope's lens fogs up because of the differential in temperature between the initial temperature of the probe and the interior of the human body. The optical scope is much cooler than the warm and moist interior of the human body. This temperature differential produces a moist film on the lens of the optical scope, resulting in the clouding of the lens.

When the lens fogs up, a surgeon must wait several minutes, with the optical scope being inserted into the interior of the body, until the temperature of the optical scope is equalized with the temperature of the interior of the body. This is a waste of precious time and prolongs the length of the surgery. Therefore, a simple, safe, sterile and inexpensive method and apparatus is needed to prevent the lens of the optical scope from fogging up. The present invention provides such a device.

One known prior art teaching of a solution to the aforementioned deficiency and shortcoming is to coat the lens of the optical scope with an anti-fogging material prior to inserting the scope into the incision. To date, the results from this prior art technique have been marginal at best. Other prior art references that discuss subject matter that bears some relation to matters discussed herein are U.S. Pat. No. 5,207,213 to Auhll et al. (Auhll), U.S. Pat. No. 4,279,246 to Chikama (Chikama), U.S. Pat. No. 5,400,767 to Murdoch (Murdoch), U.S. Pat. No. 5,549,543 to Kim (Kim), and U.S. Pat. No. 5,647,840 to D'Amelio et al. (D'Amelio).

Auhll discloses a laparoscope for performing laparoscopic surgery. The laparoscope includes a rigid elongated sheath tube having a distal section and a proximal section. The distal section has a distal tip with a lens. The lens has an exterior surface located at the distal tip. The laparoscope includes a fluid flow channel which terminates in a nozzle located at the distal tip for directing a fluid flow across the exterior surface of the lens. The laparoscope further includes a first channel which terminates in an orifice which is capable of directing a flow of irrigation fluid along a selected path. Auhll does not teach or suggest a simple method for preventing the formation of moisture film on the lens of an optical scope. Auhll merely discloses a complicated apparatus for removing the moisture film by directing a fluid over the optical scope.

Chikama disclose a device for preventing the clouding of an observing window of an optical scope using heat rays from a light source. A converter is provided for changing light into heat and transmitting optical bundles. A portion of the light is changed into heat by the converter causing the observing window to be warmed, thereby preventing the clouding. Although Chikama discloses a method and apparatus for heating the lens of an optical scope. Chikama does not use a simple, disposable sheath to warm the optical scope. Chikama utilizes a complicated device having a light source, to generate the necessary heat. Murdoch discloses a device for cleaning the lens of an optical scope within removing the scope from the body cavity. The device includes a tube, an inner diameter of the tube accepting the shaft of the optical scope. On the inner circumference, near to or at one end of the tube, is a ridge that can direct a flow of fluid within the tube onto the lens of the optical scope. During operation, whenever the lens becomes obscured, a fluid is injected into the device to clean the lens. Murdoch does not teach or suggest a device to prevent the formation of a moisture film on the lens of the optical scope. Murdoch merely discloses a device to remove a film obscuring the lens of the optical scope.

Kim discloses a laparoscopic defogging apparatus used to regulate and maintain the temperature of a lens at an end portion of the laparoscope. The apparatus utilizes a receptacle containing a first sterile fluid in which the lens is placed within. Additionally, a container is provided into which the receptacle is placed, the container being adapted to receive and contain a second sterile fluid at a sufficient depth to provide thermal contact with at least a part of the receptacle side wall portion. Kim also includes a heating device which provides heat to the sterile fluids whereby the laparoscope is maintained at a constant desired temperature. Although Kim discloses a device which warms the lens of an optical scope, Kim does not teach or suggest a simple method for heating the lens. Rather, Kim utilizes a complicated device using fluids to maintain the lens of the optical scope at the desired temperature.

D'Amelio discloses an endoscope having a distally heated lens for performing laparoscopic surgery. The laparoscope includes a rigid elongated sheath tube which encloses means defining a fiber optic light caring bundle. The fiber optic bundle has a proximal end which is adapted to be operatively coupled to a light source having light energy including infrared radiation and a distal end which is located in the distal section of the sheath tube contiguous the distal lens. The lens is heated by the light source. D'Amelio does not teach or suggest a device which can be simply and effectively used on an existing optical scope. D'Amelio merely discloses designing an entirely new and more complicated optical scope to prevent the formation of an film obscuring the lens of the optical scope.

Additionally, other methods have been used to solve the problem of moisture film formation. One such method involves applying alcohol wipes to the lens prior to use within the interior of the body. However, the alcohol wipes do not prevent the formation of the moisture film. Since the alcohol is cool, the lens remains cool, resulting in the formation of the unwanted film.

Thus, it would be a distinct advantage to have a method and apparatus for heating an optical instrument to prevent the fogging of the lens of the optical instrument. It is an object of the present invention to provide such a method and apparatus.

SUMMARY OF THE INVENTION

The present invention is an instrument heater for heating an optical scope used in laparoscopic surgery. The instrument heater may also be used to heat other surgical instruments. The instrument heater includes a sheath surrounding the instrument. The sheath has an inner wall forming a bore for receiving the instrument and an outer wall forming a void between the inner wall and the outer wall. Between the inner and outer walls of the sheath is a chemical solution, such as food grade sodium acetate and water, which is reactive to a chemical substance for generating heat. On one end of the sheath is a closed-ended tip. The tip includes an activator disk having a substance, such as garnet powder, attached to the activator disk. When the activator disk is flexed, the chemical substance is ejected from the activator disk which mixes with the chemical solution. The interaction of the chemical solution and the chemical substance results in an exothermic reaction which generates heat within the sheath. On the opposite end of the sheath is an opening for receiving the optical scope within the bore. The instrument is inserted within the opening into the bore, being surrounded by the inner wall of the sheath. When the instrument requires heating, the activator disk is flexed causing the generation of heat within the sheath, which is then transmitted to the instrument.

The invention includes a method of heating an instrument used in laparoscopic surgery. The method begins by flexing an activator disk located on an end of a sheath of the instrument heater. Next, the sheath forming a bore is placed on the instrument heater. The flexing of the activator disk causes an exothermic reaction in the sheath having a chemical solution. The resulting exothermic reaction generates heat within the sheath. Next, the optical scope is heated by the sheath. The instrument heater is then removed from the instrument.

DETAILED DESCRIPTION OF EMBODIMENTS

The present invention is a method and apparatus for heating a surgical instrument, such as an optical scope used in laparoscopic surgery.

Figure 1:
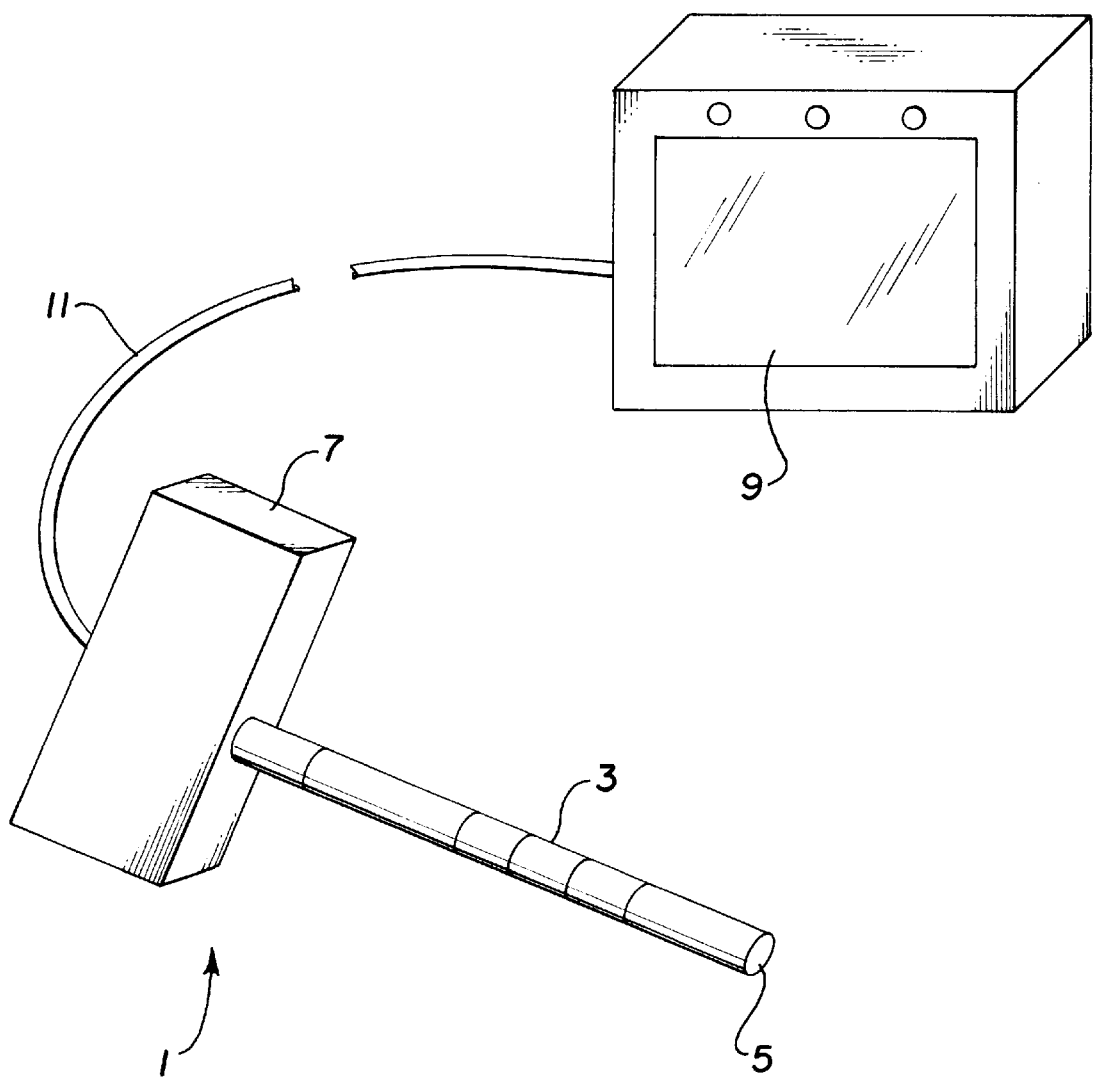
FIG. 1 is a front perspective view of an optical scope used in laparoscopic surgery.

FIG. 1 is a front perspective view of an optical scope 1 used in laparoscopic surgery. The optical scope 1 includes a long cylindrical probe 3. The probe 3 is very thin and typically has a length of several inches. At one end of the probe 3 is a lens 5. The lens 5 is constructed of a clear material. On an opposite end of the probe 3 is a camera 7 used in televising the image received from the lens 5. Normally, a fiber optic cable (not shown) is utilized to connect the camera 7 to the lens 5. The camera 7 is attached to a monitor 9 by a cable 11. The monitor 9 is used to display the images received by the camera 7. The optical scope 1 may be a laparoscope, endoscope, coeloscope or similar telescope.

In operating the optical scope 1, a small incision is made through the skin of a human body. The probe 3 is inserted several inches into the interior of the body. The camera 7 remains outside of the body. The lens 5 is position for viewing a specific area desired by the surgeon. The images received by the lens 5 are then transmitted to the camera 7 and displayed on the monitor 9.

Prior to entering the body, the probe 3 is normally at room temperature, which is several degrees cooler than the temperature of a human body. When the probe 3 is inserted into the body, the probe 3 normally is obscured by a moisture film which develops upon the lens 5. The moisture film develops because the temperature of the probe 3 is several degrees cooler than the body. Additionally, the interior of a human body is very moist, causing moisture to develop on the cooler surface of the lens 5. This moisture film remains on the lens 5 until the probe 3 and its lens 5 warm to a temperature near that of the interior of the body. This temperature equalization process normally takes several minutes. Precious time is lost in waiting for the lens 5 of the optical scope 1 to clear.

Figure 2:
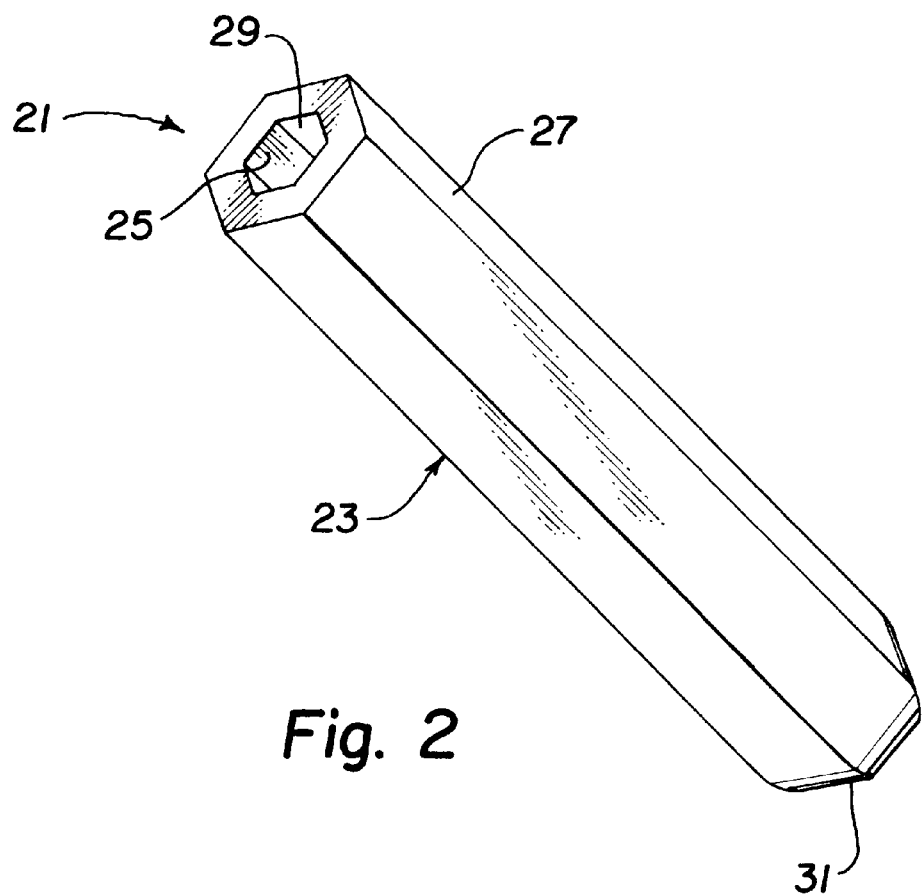
FIG. 2 is a side perspective view of an instrument heater according to the teachings of the present invention.

FIG. 2 is a side perspective view of an instrument heater 21 according to the teachings of the present invention. The instrument heater 21 is cylindrically-shaped. The instrument heater 21 includes a sheath 23. The sheath 23 has an inner wall 25 and an outer wall 27 running across the entire length of the sheath 23. The inner wall 25 and the outer wall 27 form an essentially circular bore (not shown in FIG. 1) through the center of the sheath 23. At one end of the sheath 23 is an opening 29 which serves as the beginning of the bore. At an opposite end of the sheath 23 is a tip 31. The tip 31 is closed-ended and essentially dome-shaped.

The inner wall 25 and the outer wall 27 are constructed of a flexible nonporous material allowing for the insulation of heat. In the disclosed embodiment, the material is chip board which is a thin cardboard type material which insulates the heat within the interior of the sheath 23. However, any flexible and nonporous material capable of being sterilized may be used.

Between the inner wall 25 and the outer wall 27 is a chemical solution used in forming an exothermic reaction to create heat. In the disclosed invention, a food grade sodium acetate and water solution is utilized. Other chemical solutions may be used such as calcium chloride and water to produce the desired heat. The mixed chemical solution runs between the inner wall 25 and the outer wall 27 across the entire length of the sheath 23. Additionally, the chemical solution is present at the tip 31. The inner wall 25 and the outer wall 27 retain the chemical solution within the sheath 23.

Figure 3:
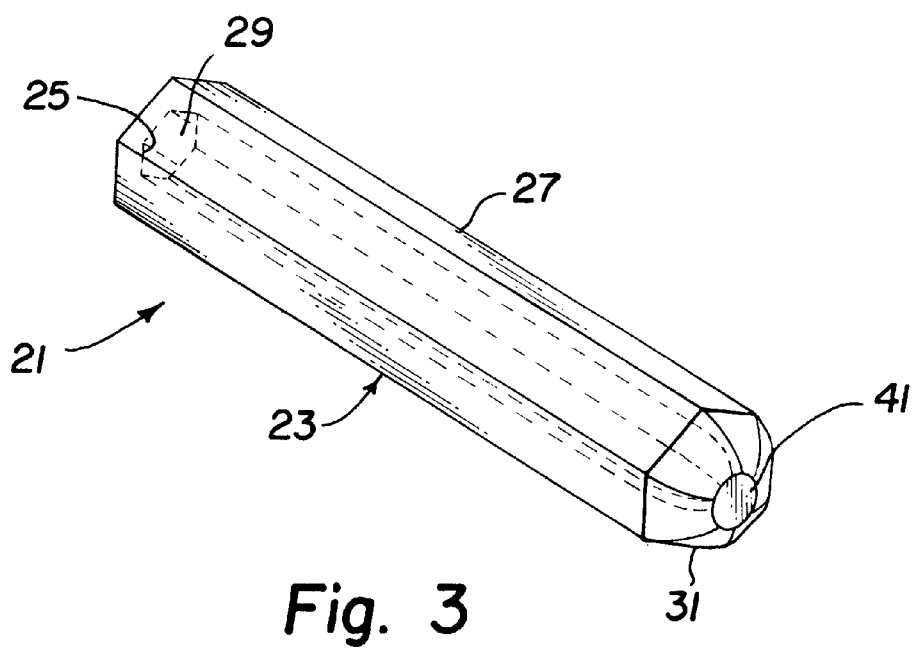
FIG. 3 is a cut-away perspective view of the instrument heater according to the teachings of the present invention.

FIG. 3 is a cut-away perspective view of the instrument heater 21 according to the teachings of the present invention. Between the inner wall 25 and the outer wall 27 at the tip 31 is an activator disk 41. The activator disk 41 is described in U.S. Pat. No. 4,872,442 to Manker and is hereby incorporated herein by reference. The activator disk 41 is located between inner wall 25 and the outer wall 27 at the tip 31 and surrounded by the chemical solution.

Figure 4:
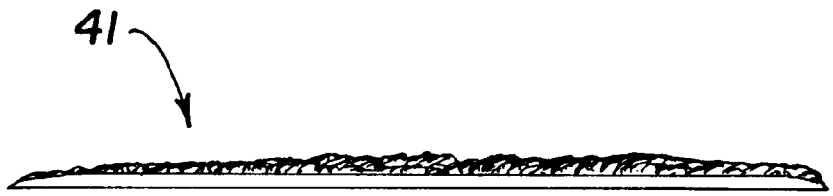
FIG. 4 is a side view of the activator disk according to the teachings of the present invention.
Figure 5:
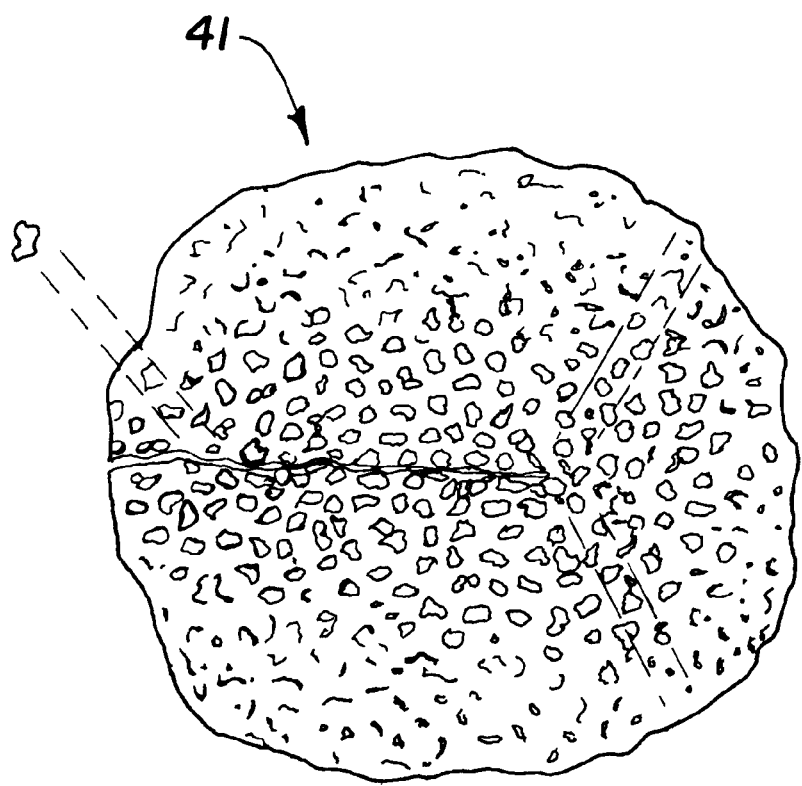
FIG. 5 is a greatly enlarged graphically illustrative view of a portion of the surface of the activator disk according to the teachings of the present invention.

FIG. 4 is a side view of the activator disk 41 according to the teachings of the present invention. FIG. 5 is a greatly enlarged graphically illustrative view of a portion of the surface of the activator disk 41 according to the teachings of the present invention. The activator disk has a plurality of slits (not shown) in a flexible metal article. The opposing sides of the slits are in contact along at least a part of the length of the slit, and by an eroded and roughened surface on the metal article which includes a number of minute metal nodules attached to and protruding from the surface. The nodules are adapted to be detached or broken-off upon flexing of the activator disk 41. Such flexing is believed to cause a metal-to-metal contact between the adjacent sides to release one or more minute particles of metal, such as garnet powder, from the roughened surface which acts as a nesting side for a crystal deposited from the solution, thereby destabilizing the chemical solution and causing it to progress rapidly from a liquid to crystalline state with a resultant generation of heat. In the disclosed invention, sodium acetate and water forms the chemical solution which is present in the sheath 23. The amount and mix of the sodium acetate with the water and its interaction with the activator disk 41 determines the amount of heat produced. The preferred temperature is approximately 104 degrees Fahrenheit. However, a temperature range of 97 to 108 degrees Fahrenheit may be utilized with the instrument heater 21. The higher end of the temperature range is necessary because any hotter of a temperature may result in damage to any portion of the body which comes in contact with the probe 3. The lower end of the temperature range is the lowest temperature in which the instrument heater 21 can be useful in preventing the formation of a moisture film upon the lens 5.

Figure 6:
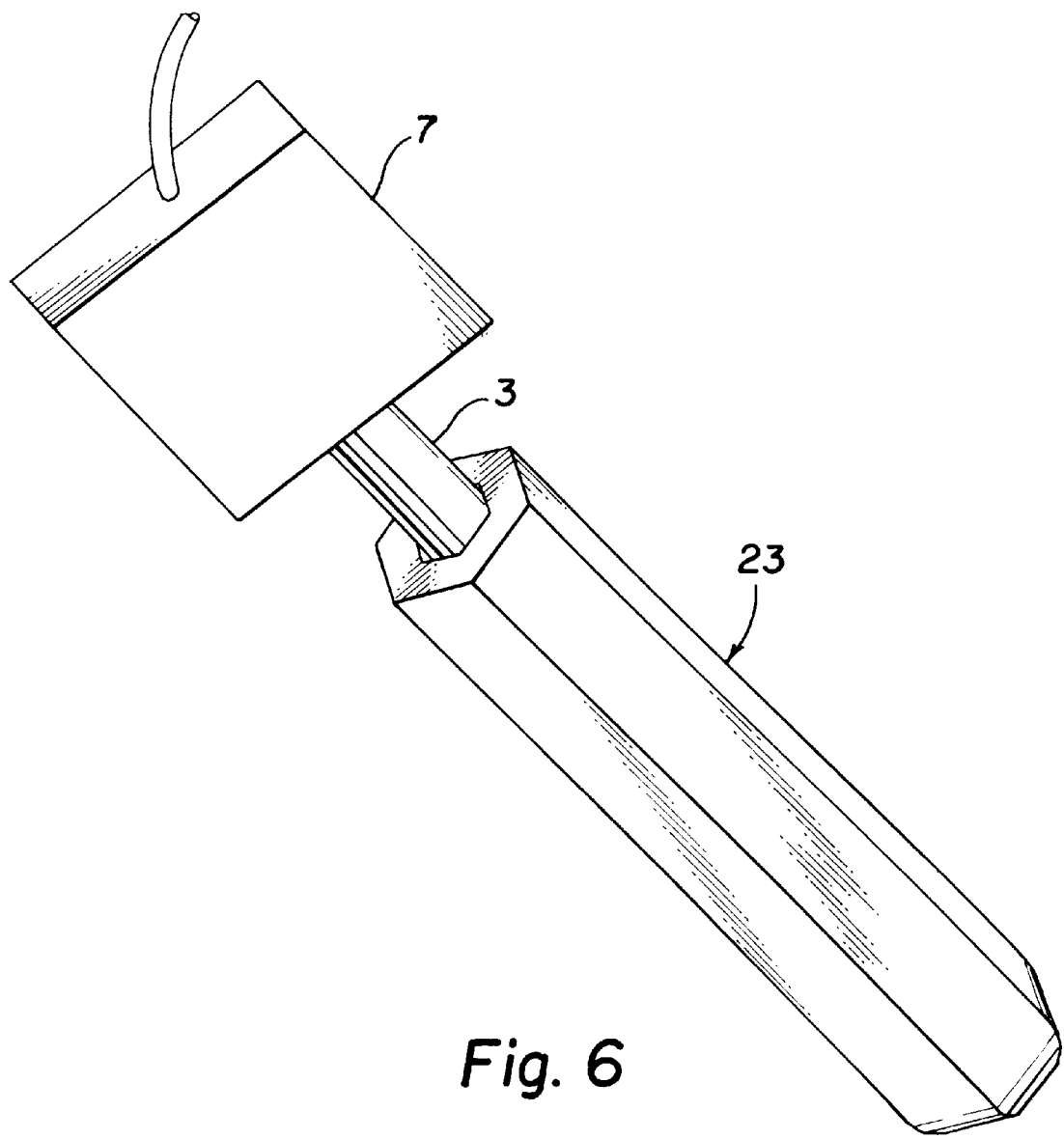
FIG. 6 is a perspective view of the instrument heater positioned on the optical scope according to the teachings of the present invention.

FIG. 6 is a perspective view of the instrument heater 21 positioned on the optical scope 1 according to the teachings of the present invention. Referring to FIGS. 1–6, the operation of the instrument heater 21 will now be explained. The instrument heater 21 is sterilized prior to use. Normally, the sterilization of the instrument heater 21 is accomplished by bombarding the instrument heater 21 with Gamma-rays. The instrument heater 21 is then vacuumed sealed and wrapped in a sterile wrap very similar to syringe packaging.

The instrument heater 21 is activated by pinching the tip 31, thereby bending the activator disk 41. Next, the instrument heater 21 is placed over the probe 3, covering several inches (approximately 4 to 6 inches) of the probe 3 as well as the lens 5. Upon flexing the activator disk 41, the activator disk 41 releases metal nodules which react with the sodium acetate to cause an exothermic reaction at approximately 104 degrees Fahrenheit. This exothermic reaction heats the sheath 23 which transmits the heat to the probe 3 and the lens 5. The sheath 23 may be massaged to induce a faster reaction by mixing more metal nodules into the chemical solution throughout the length of the sheath 23.

The instrument heater 21 remains in place on the probe 3 for several minutes until the probe 3 and its lens 5 are at a temperature approximately equal to the interior of a human body. Once this temperature is reached, the instrument heater 21 is removed from the probe 3 and discarded. The probe 3 and the lens 5 are then inserted into the body for examination of the interior of the body.

The sheath 23 runs approximately 4 to 6 inches to cover most of the probe 3 and lens 5. The probe 3 as well as the lens 5 should both be heated. If the lens 5 was only heated, the cool probe 3 may cool the lens 5 back to a lower temperature, resulting in the formation of a moisture film upon the lens 5.

In alternate embodiments of the present invention, the instrument heater 21 may be used to heat other surgical instruments such as clamp, forceps, or scalpels.

Figure 7:
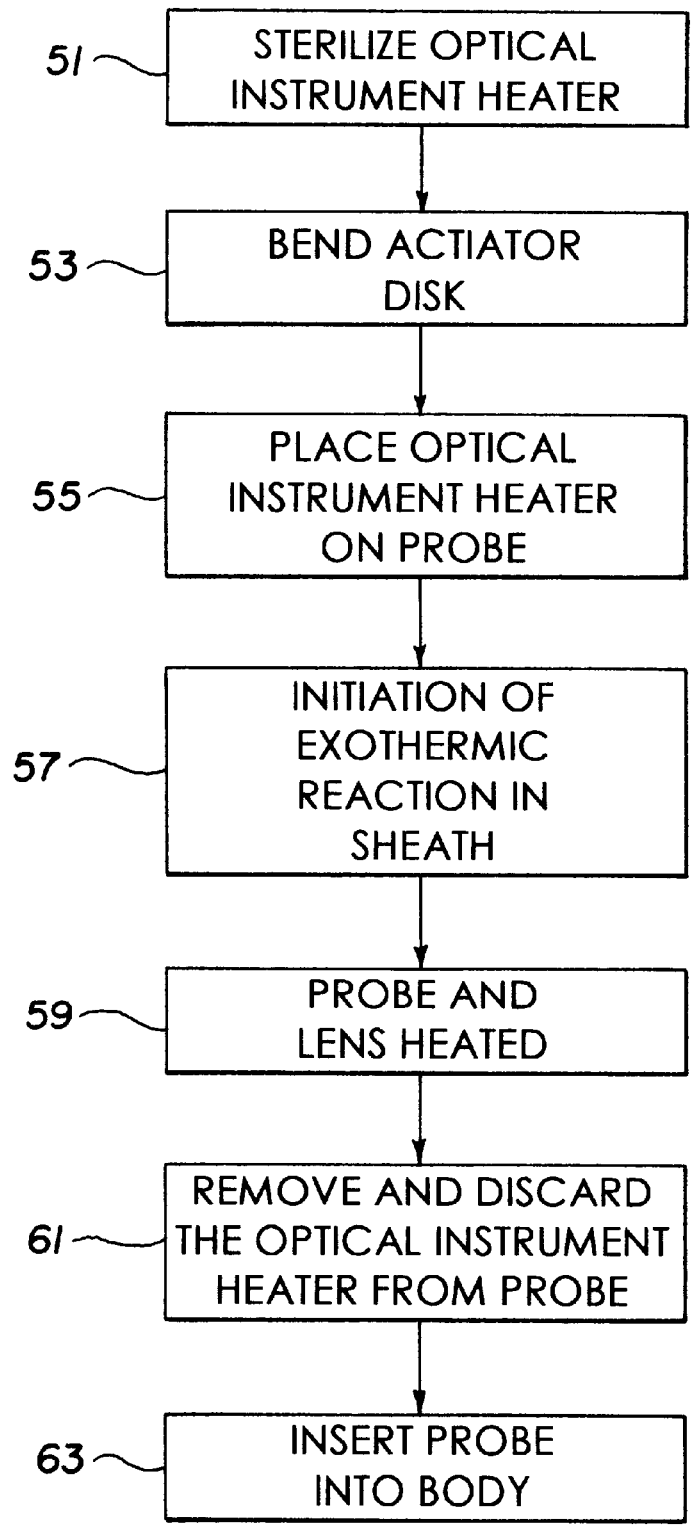
FIG. 7 is a flow chart illustrating the steps of heating an optical scope according to the teachings of the present invention.

FIG. 7 is a flow chart illustrating the steps of heating an optical scope 1 according to the teachings of the present invention. The method starts with step 51 where the instrument heater 21 is sterilized. Sterlization normally occurs by bombarding the instrument heater 21 with Gamma-rays. Next, in step 53, the activator disk 41 is bent, releasing metal nodules into the chemical solution (food grade sodium acetate in the disclosed invention) contained in the sheath 23. The activator disk 41 is bent by pinching the tip 31. In step 55, the instrument heater 21 is placed on the probe 3 with the sheath 23 covering the lens 5 and several inches of the probe 3.

Next, in step 57, the interaction of the metal nodules with the chemical solution initiates an exothermic reaction which radiates heat throughout the sheath 23. In step 59, the radiated heat in the sheath 23 is transmitted to the probe 3 and the lens 5. In step 61, when the desired temperature for the probe 3 and lens 5 is reached, the instrument heater 21 is removed and may be disposed. In step 63, the heated probe 3 and lens 5 is then inserted into a body. Since the lens 5 has the same or nearly the same temperature as within the body, a moisture film will not form over the lens 5. Therefore, viewing of the desired area within the body's interior can start immediately.

In alternate embodiments, the present invention may be used in dentistry for such tools as an extended mirror and in veterinary medicine with surgical tools used on animals.

The instrument heater 21 offers many advantages. The instrument heater is a simple, inexpensive, and disposable means for solving the problem of the formation of a moisture film upon the lens of the optical scope. The instrument heater provides an effective means for heating the optical scope without modifying an existing optical scope. Additionally, sterilization of the instrument heater is maintained easily by initially sterilizing the instrument heater with Gamma-rays and vacuum sealing the instrument heater in a sterile wrap. After use, the instrument heater can be discarded, thereby removing the problem of having to re-sterilize the instrument heater.

What is claimed is:

1. An instrument heater for heating an instrument comprising:
    a sheath capable of surrounding the instrument, the sheath having:
        an inner wall forming a bore adapted for the instrument;
        an outer wall forming a void between the inner wall and the outer wall;
        a chemical solution filling the void between the outer wall and the inner wall; and
        a first end forming an opening for receiving the instrument; and
    an activator disk attached between the inner wall and the outer wall of the sheath, the activator disk having a substance, whereby the activator disk expels the substance when flexed causing an interaction of the substance with the chemical solution, the interaction of the substance and the chemical solution generating heat within the sheath.

2. The instrument heater of claim 1 further comprising a closed-ended tip integrally connected to a second end of the sheath and wherein the activator disk is located within the closed-ended tip.

3. The optical instrument heater of claim 1 wherein the chemical solution includes sodium acetate and water.

4. The optical instrument heater of claim 1 wherein the chemical solution includes calcium chloride and water.

5. The optical instrument heater of claim 1 wherein the substance includes metal nodules reactive to the chemical solution.

6. The optical instrument heater of claim 1 wherein the inner wall is constructed of chip board.

7. The optical instrument heater of claim 1 wherein the outer wall is constructed of chip board.

8. The optical instrument heater of claim 1 wherein the heat generated by the interaction of the chemical solution and the chemical substance is approximately 104 degrees Fahrenheit.

9. A method of heating a surgical instrument, the method comprising the steps of:

bending an activator disk located within a sheath of an instrument heater;

placing the sheath forming a bore on the instrument;

initiating an exothermic reaction in the sheath;

heating the instrument by the exothermic reaction within the sheath; and removing the instrument heater from the instrument.

10. The method of heating an instrument of claim 9, further comprising, before the step of placing an instrument heater on the instrument, the step of sterilizing the instrument heater.

11. The method of heating an instrument of claim 10, wherein the step of sterilizing the instrument heater includes bombarding the instrument heater with Gamma-rays and vacuum sealing the instrument heater within a sterile wrap.

12. The method of heating an instrument of claim 9, further comprising, after the step of removing the instrument heater from the instrument, the step of inserting the instrument into a human body.

13. The method of heating an instrument of claim 9, wherein the step of initiating an exothermic reaction includes interacting a substance ejected from the activator disk with a chemical solution filled between an inner wall and an outer wall of the sheath.

14. The method of heating an optical scope of claim 13, wherein the step of interacting a substance ejected from the activator disk with a chemical solution filled between the inner wall and the outer wall includes mixing sodium acetate and water filled between the inner wall and outer wall and metal nodules ejected from the activator disk.

15. The method of heating an optical scope of claim 13, wherein the step of interacting a substance ejected from the activator disk with a chemical solution filled between the inner wall and the outer wall includes mixing calcium chloride and water filled between the inner wall and outer wall and metal nodules ejected from the activator disk.

16. The method of heating an instrument of claim 9, further comprising, after the step of removing the instrument heater from the instrument, the step of inserting the instrument into an animal.

17. The method of heating an instrument of claim 9, further comprising, after the step of removing the instrument heater from the instrument, the step of inserting the instrument into a mouth of a human.

* * * * *

UNITED STATES PATENT AND TRADEMARK OFFICE
CERTIFICATE OF CORRECTION

PATENT NO. : 5,910,106
DATED : June 8, 1999
INVENTOR(S) : Shanon Morgan, Michael W. Keith, Kevin P. Nelms, and David Mills It is certified that error appears in the above-indentified patent and that said Letters Patent is hereby corrected as shown below:

In Column 2, Line 48, please replace "caring", and substitute therefor ---carrying---.

Signed and Sealed this

Second Day of November, 1999

Attest:

Attesting Officer

Q. TODD DICKINSON

Acting Commissioner of Patents and Trademarks